(12) United States Patent
Sørensen et al.

(10) Patent No.: US 11,341,691 B2
(45) Date of Patent: May 24, 2022

(54) EXTRACTION OF A BIAS FIELD INVARIANT BIOMARKER FROM AN IMAGE

(71) Applicant: Biomediq A/S, Copenhagen (DK)

(72) Inventors: Lauge Sørensen, Copenhagen (DK); Mads Nielsen, Dragør (DK); Christian Igel, Frederiksberg (DK)

(73) Assignee: CEREBRIU A/S, Copenhagen (DK)

( * ) Notice: Subject to any disclaimer, the term of this patent is extended or adjusted under 35 U.S.C. 154(b) by 12 days.

(21) Appl. No.: 15/572,676

(22) PCT Filed: May 12, 2016

(86) PCT No.: PCT/EP2016/060787
§ 371 (c)(1),
(2) Date: Nov. 8, 2017

(87) PCT Pub. No.: WO2016/180954
PCT Pub. Date: Nov. 17, 2016

(65) Prior Publication Data
US 2018/0137655 A1 May 17, 2018

(30) Foreign Application Priority Data
May 13, 2015 (GB) .................................. 1508141.7

(51) Int. Cl.
*G06T 11/00* (2006.01)
*G06T 7/44* (2017.01)
(Continued)

(52) U.S. Cl.
CPC .......... *G06T 11/005* (2013.01); *A61B 5/0042* (2013.01); *A61B 5/055* (2013.01); *A61B 5/4088* (2013.01); *A61B 5/7225* (2013.01); *G06K 9/6267* (2013.01); *G06T 7/0012* (2013.01); *G06T 7/44* (2017.01); *G06V 10/443* (2022.01);
(Continued)

(58) Field of Classification Search
None
See application file for complete search history.

(56) References Cited

U.S. PATENT DOCUMENTS

| 8,811,724 B2 | 8/2014 | Nielsen et al. |
| 9,092,691 B1* | 7/2015 | Beaumont ............. G06T 7/0014 |
| 2013/0204115 A1* | 8/2013 | Dam ...................... A61B 5/055 |
| | | 600/410 |

OTHER PUBLICATIONS

Robustness of Local Binary Patterns in Brain MR Image Analysis. Unay et al. Aug. 2007.*

(Continued)

*Primary Examiner* — Delomia L Gilliard
(74) *Attorney, Agent, or Firm* — IPro, PLLC

(57) ABSTRACT

The present invention provides a method of computer analysis of a data set representing an image to extract a texture based measure therefrom, said image including a multiplicative bias in intensity within the image of unknown magnitude, the method comprising applying to said data set a bank of texture extracting filters, such that said filters are chosen from filters that are invariant to the presence of a multiplicative bias field. By providing such a method, rather than attempting to correct the bias field before extraction of a texture based-biomarker, a texture-based biomarker that is bias field invariant is extracted. This makes correction of the bias field unnecessary.

23 Claims, 1 Drawing Sheet

(51) Int. Cl.
G06K 9/62 (2022.01)
G06V 10/44 (2022.01)
G06V 20/69 (2022.01)
A61B 5/00 (2006.01)
A61B 5/055 (2006.01)
G06T 7/00 (2017.01)

(52) U.S. Cl.
CPC .... *G06V 20/69* (2022.01); *G06T 2207/10088* (2013.01); *G06T 2207/20012* (2013.01); *G06T 2207/20024* (2013.01); *G06T 2207/20064* (2013.01); *G06T 2207/20081* (2013.01); *G06T 2207/30016* (2013.01)

(56) References Cited

OTHER PUBLICATIONS

Local MRI analysis approach in the diagnosis of early and prodromal Alzheimer's disease. Chincarini et al. (Year: 2011).*
Texture Features from Mammographic Images and Risk of Breast Cancer. Manduca et al. (Year: 2009).*
Belaroussi, B., et al., Intensity non-uniformity correction in MRI: existing methods and their validation. Med Image Anal, 2006. 10(2): p. 234-46.
Sled, J.G., A.P. Zijdenbos, and A.C. Evans, A nonparametric method for automatic correction of intensity nonuniformity in MRI data. IEEE Trans Med Imaging, 1998. 17(1): p. 87-97.
Chincarini, A., et al., Local MRI analysis approach in the diagnosis of early and prodromal Alzheimers disease. Neuroimage, 2011. 58(2): p. 469-480.
Chincarini, A., et al., Automatic temporal lobe atrophy assessment in prodromal AD: Data from the DESCRIPA study. Alzheimers Dement, 2014. 10(4): p. 456-67.
S rensen, L., et al., Texture-Based Analysis of COPD: A Data-Driven Approach. IEEE Trans Med Imaging, 2012. 31 (1): p. 70-78.
Lindeberg, T., Scale Space, in Encyclopedia of Computer Science and Engineering. 2009, John Wiley and Sons. p. 2495-2504.
Ojala, T., M. Pietik inen, and D. Harwood, A comparative study of texture measures with classification based on featured distributions. Pattern Recognit, 1996.29(1): p. 51-59.
Cortes, C. and V. Vapnik, Support-Vector Networks. Mach Learn, 1995. 20(3): p. 273-297.
Jaakkola, T., M. Diekhans, and D. Haussler. Using the Fisher kernel method to detect remote protein homologies, in ISMB. 1999. AAAI Press.
Wyman, B.T., et al., Standardization of analysis sets for reporting results from ADNI MRI data. Alzheimers Dement, 2013. 9(3): p. 332-337.
Braak, H. and E. Break, Frequency of stages of Alzheimer-related lesions in different age categories. Neurobiol Aging, 1997. 18(4): p. 351-357.
West, M.J., et al., Differences in the pattern of hippocampal neuronal loss in normal ageing and Alzheimers disease. Lancet, 1994. 344(8925): p. 769-772.
Fischl, B., et al., Whole brain segmentation: automated labeling of neuroanatomical structures in the human brain. Neuron, 2002. 33(3): p. 341-355.
DeLong, E.R., D.M. DeLong, and D.L. Clarke-Pearson, Comparing the areas under two or more correlated receiver operating characteristic curves: a nonparametric approach. Biometrics, 1988.44(3): p. 837-845.
Porwik P., Lisowska A., The Haar-Wavelet Transform in Digital Image Processing: Its Status and Achievements, Machine Graphics and Vision, vol. 13, No. 1/2, pp. 79-98, 2004.
Turner, M.R., Texture discrimination by Gabor functions. Biol Cybern, 1986. 55(2-3): p. 71-82.
Ojala, T., et al., Multiresolution Gray-Scale and Rotation Invariant Texture Classification with Local Binary Patterns. IEEE Trans Pattern Anal Mach Intell, 2002. 24(7): p. 971-987.
Petersen, R.C., Mild cognitive impairment as a diagnostic entity. J Intern Med, 2004. 256(3): p. 183-194.

* cited by examiner

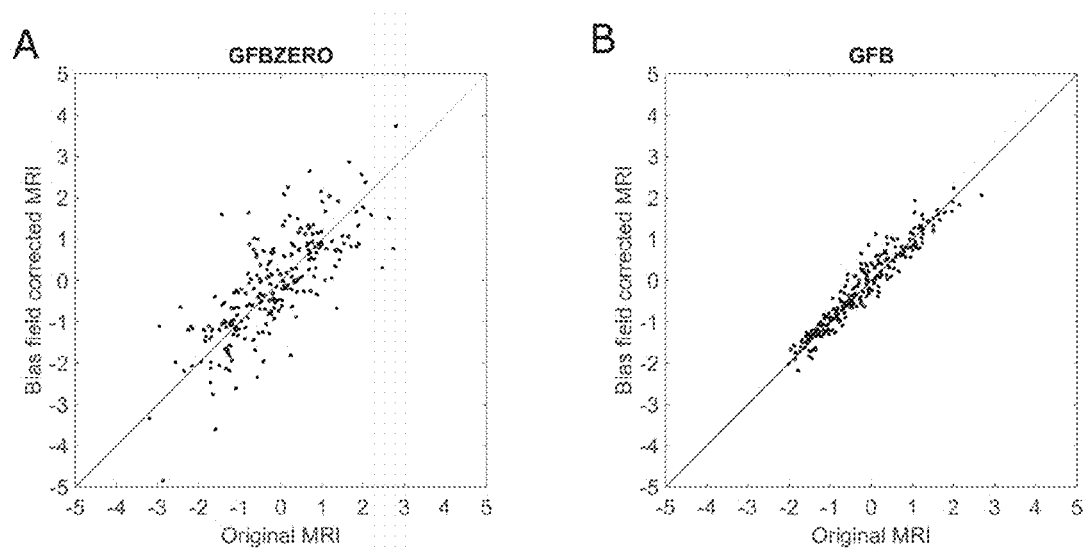

EXTRACTION OF A BIAS FIELD INVARIANT BIOMARKER FROM AN IMAGE

The present invention relates to methods for the computer analysis of data sets representing images in which there may be a multiplicative intensity bias field of unknown magnitude within each image. The invention has particular, but not exclusive, relevance to processing magnetic resonance images (MRI) images.

Structural MRI is a non-invasive technique for examining the physical structure of the brain. The extraction of textural information in the brain tissue may enable the computation of a prognostic biomarker that differentiates between cases of mild cognitive impairment (MCI) that over time will progress or which will not progress to Alzheimer's disease (AD).

Successful determination of which patients are likely to progress from MCI to AD will enable selection of patients for clinical trials of potential disease-modifying treatments for AD, whether in the form of medicaments or other forms such as diet or behavioural modification, in such a way as to increase the power of the trial by removing patients who would not progress to AD irrespective of treatment.

This is of high value in evaluating the utility of candidate treatments by determining whether such a treatment prevents progression in those cases in which the biomarker predicts that progression is likely.

A texture-based biomarker consists of a texture descriptor, a high-dimensional representation that characterizes the image texture, and which can be used in a trained classifier that maps an instance of the texture descriptor to a decision, e.g., "disease" or "disease with a probability of x". Such a texture descriptor can be applied in the characterization of brain tissue texture in MRI.

MRI images are affected by bias fields that can potentially influence the texture descriptor. In order to avoid this, bias fields are normally corrected algorithmically prior to subsequent processing, and a multiplicative bias field is commonly assumed in the correction methods [1, 2]. However, the corrections may be imperfect and the problem persisting.

MRI texture-based biomarker extraction has previously been proposed for application to the hippocampus in MRI images for prediction of conversion from MCI to AD [3, 4] with promising results. The descriptor in that method was based on 7 different filters, and 6 out of these (raw intensity, mean, Gaussian mean, range, standard deviation, entropy) would be affected by multiplicative bias fields. For example, the intensity standard deviation in a region will decrease/increase for multiplicative factors smaller/larger than 1, and the intensity histogram will probably change for factors sufficiently smaller/larger than 1 (dependent on the fixed intensity binning) causing a change in entropy. The descriptor used in [3, 4] is therefore multiplicative bias field variant, and an algorithmic bias field correction is applied prior to texture descriptor computation.

Rather than attempting to correct the bias field before extraction of a texture based-biomarker, in this invention we extract a texture-based biomarker that is bias field invariant. This makes correction of the bias field unnecessary, although of course it can still optionally be performed.

Accordingly, the present invention now provides a method of computer analysis of a data set representing an image to extract a texture based measure therefrom, said image including a multiplicative bias in intensity within the image of unknown magnitude, the method comprising applying to said data set a bank of texture extracting filters, such that said filters are chosen from filters that are invariant to the presence of a multiplicative bias field. Optionally in such a method, a texture extracting filter applied in said method is one of three eigenvalues of the Hessian matrix defined by:

$$\lambda_i(x;\sigma) \ i=1,2,3, \ |\lambda_1| \geq |\lambda_2| \geq |\lambda_3|$$

where $x=[x, y, z]^T$ is a voxel, $\sigma$ is the scale at which the filter is applied and the Hessian matrix is defined as $$H(x;\sigma) = \begin{bmatrix} I_{xx,\sigma} & I_{xy,\sigma} & I_{xz,\sigma} \\ I_{xy,\sigma} & I_{yy,\sigma} & I_{yz,\sigma} \\ I_{xz,\sigma} & I_{yz,\sigma} & I_{zz,\sigma} \end{bmatrix};$$

Each of the three eigenvalues of the Hessian matrix may be applied as a texture extracting filter.

A texture extracting filter applied in said method may be the gradient magnitude defined by:

$$\|\nabla G(x;\sigma)\|_2 = \sqrt{I_{x,\sigma}^2 + I_{y,\sigma}^2 + I_{z,\sigma}^2}$$

A texture extracting filter applied in said method may be the Laplacian of the Gaussian defined by:

$$\nabla^2 G(x;\sigma) = \lambda_1(x;\sigma) + \lambda_2(x;\sigma) + \lambda_3(x;\sigma)$$

A texture extracting filter applied in said method may be the Gaussian curvature defined by:

$$K(x;\sigma) = \lambda_1(x;\sigma)\lambda_2(x;\sigma)\lambda_3(x;\sigma);$$

A texture extracting filter applied in said method may be the the Frobenius norm of the Hessian matrix defined by:

$$\|H(x;\sigma)\|_F = \sqrt{\lambda_1(x;\sigma)^2 + \lambda_2(x;\sigma)^2 + \lambda_3(x;\sigma)^2}.$$

Preferably, at least one said texture extracting filter is applied at multiple scales a. Suitably, at least for brain images, said scales a lie in a range from 0.3 to 25 mm, more preferably in a range from 0.3 to 2.5 mm. For microscopy images, said scales a may lie in a range from 0.3 to 25 μm.

Texture extracting filters may be applied at N scales, where N is computed using:

$$N = \frac{1}{p}\log_2\left(\frac{\sigma_{high}}{\sigma_{low}}\right) + 1$$

where p is the scale factor, $\sigma_{low}$ is the lower end of the scale range, and $\sigma_{high}$ is the upper end of the scale range.

Accordingly by way of example, from 3 to 8 texture extracting filters may be applied at from 1 to 25 scales.

The texture based measure may be obtained by concatenating histograms of filter responses obtained by applying said bank of texture extracting filters.

The histograms of filter responses may be estimated using various binning methods including fixed binning, adaptive binning, or by soft assignments as in locally orderless images.

The method may further comprise applying a statistical classifier to said texture based measure extracted from an image data set to label said image as being included in a class of images.

Generally any classifier may be used, for instance random forest (RF), linear discriminant analysis (LDA), $k^{th}$ nearest neighbour (kNN), support vector machines (SVM). In the example below an SVM with a radial Gaussian kernel (sometimes called radial basis function kernel) is used, but other kernels may be used instead, e.g. a linear kernel. Of these we prefer SVM and consider kNN to be least preferred.

In a preferred use of the invention, said data set represents a medical image and said measure is a biomarker. Preferably, said data set represents an MRI image, suitably of a brain or part thereof.

In preferred aspects of the invention, the image derives from a person with mild cognitive impairment (MCI) as defined in [19].

The method may further comprise applying a statistical classifier as described above to said texture based biomarker extracted from an MRI brain image to label said image according to a likelihood of the person progressing from MCI to dementia. Optionally, the type of dementia is Alzheimer's disease (AD).

The invention includes a computer programmed to carry out a method as described and includes also a computer program for inputting into a computer to cause the computer to carry out such a method.

The methodology described herein can be applied to the hippocampus in MRI images. However, it can also be applied to other parts of the brain in MRI images. For example, these may be amygdala, or corpus callosum or more generally the total white matter or the whole brain.

We describe below an example of the invention applied to T1 weighted MRI images but other MRI sequences than T1 weighted could be used. For example, the imaging might be T2 weighted, or proton density weighted.

Other kinds of images entirely may exhibit multiplicative bias fields. These include:
- badly calibrated computed tomography (CT) scans
- microscopy images under varying lighting conditions
- positron emission tomography (PET) scans with varying tracer retention
- X-ray scans with varying exposure The invention may be applied in these cases also. The bias in intensity of unknown magnitude may of course in a particular case actually be zero.

A texture descriptor of the invention that is invariant to multiplicative bias fields may be used for MRI texture-based prediction of MCI-to-AD conversion. This may be achieved by the combination of log-transformed MRI images (to make the image formation model additive) and, in a particular example, an adaptation of a descriptor that has previously been successfully applied in lung computed tomography [5, 6], The most important adaptation to the descriptor described there is the exclusion of the Gaussian function, the only filter in the descriptor that is not multiplicative invariant when considering the additive image model. The remaining 7 filters used in that descriptor are all Gaussian derivative-based and therefore multiplicative invariant under the assumption that the bias field is smooth and locally constant.

In a preferred embodiment of the invention, as practised on MRI images, the texture within a region of interest (ROI) may be characterized using filter response histograms of a 3-dimensional, rotation-invariant, multi-scale Gaussian derivative-based filter bank. In the following, $I_{x,\sigma}$ and $I_{xx,\sigma}$ denote the partial first- and second-order derivative, respectively, of image I w.r.t. x at scale σ. Partial derivatives of the image at the different scales in the multi-scale representation of the image are in all cases computed using Gaussian derivatives [7], for example, $I_{x,\sigma} = I * G_{x,\sigma}$ where * denotes convolution and $G_{x,\sigma}$ is the partial first-order derivative of the Gaussian function $$G(x, \sigma) = \frac{1}{((2\pi)^{1/2}\sigma)^3} \exp\left(-\frac{\|x\|_2^2}{2\sigma^2}\right),$$

w.r.t. x at scale σ. This way of defining derivatives in scale-space makes the computation of image derivatives well-posed [7]. The filter bank may comprise a plurality of filters made up of several base filters at a number of different scales, for example a total of twenty-eight filters comprising seven base filters at four different scales (σ=0.6, 0.85, 1.2, 1.7 mm). The base filters described here measure various aspects of the local image structure, and they may be the following:

1-3) each of the three eigenvalues of the Hessian matrix $\lambda_i(x;\sigma)$, $i=1,2,3$, $|\lambda_1| \geq |\lambda_2| \geq |\lambda_3|$ where $x=[x, y, z]^T$ is a voxel and the Hessian matrix is defined as $$H(x;\sigma) = \begin{bmatrix} I_{xx,\sigma} & I_{xy,\sigma} & I_{xz,\sigma} \\ I_{xy,\sigma} & I_{yy,\sigma} & I_{yz,\sigma} \\ I_{xz,\sigma} & I_{yz,\sigma} & I_{zz,\sigma} \end{bmatrix};$$

4) the gradient magnitude $\|\nabla G(x;\sigma)\|_2 = \sqrt{I_{x,\sigma}^2 + I_{y,\sigma}^2 + I_{z,\sigma}^2}$;

5) Laplacian of the Gaussian $\nabla^2 G(x;\sigma) = \lambda_1(x;\sigma) + \lambda_2(x;\sigma) + \lambda_3(x;\sigma)$;

6) Gaussian curvature $K(x;\sigma) = \lambda_1(x;\sigma)\lambda_2(x;\sigma)\lambda_3(x;\sigma)$;

and 7) the Frobenius norm of the Hessian matrix $\|H(x;\sigma)\|_F = \sqrt{\lambda_1(x;\sigma)^2 + \lambda_2(x;\sigma)^2 + \lambda_3(x;\sigma)^2}$.

Of course a different number of base filters may be employed, which may be more or less than seven, and a different number of scales may be used, which may be more or less than four.

The histogram of filter responses inside the ROI in a filtered MRI image may be estimated as $$h_F(i, I) = \frac{\sum_{x \in S} \delta_i(I_F(x))}{|S|}, \quad i = 1, \ldots, N_b$$

where S is the ROI, $I_F$ is a filtered version of I, $N_b$ is the number of histogram bins, and $\delta_i(x)$ is an indicator function defined as $$\delta_i(t) = \begin{cases} 1 & \text{if } t_i < t < t_{i+1}, \\ 0 & \text{otherwise} \end{cases}$$

where $t_i$ is a histogram bin edge. The edges may be determined using adaptive binning [8]; $t_i$ is the $(i-1)/N_b \times$ 100th percentile filter response in the training set. The final hippocampal texture descriptor may be obtained by concatenating the filter response histograms;

$$[h_{\lambda_1(x;0.6)}, \ldots, h_{\|H(x;0.6)\|_F}, \ldots, h_{\|H(x;1.7)\|_F}].$$

It is common to assume a smooth, multiplicative intensity bias field [1, 2]

$$I(x)=U(x)B(x),$$

where I is the observed MRI image, U is the true, unobserved image, and B is the bias field. The image formation model is made additive by taking the logarithm $$\log(I(x))=\log(U(x))+\log(B(x)),$$

and the partial (log) image derivative at scale σ w.r.t. x will then be $$\frac{\partial G(x,\sigma)}{\partial x} * \log(I(x)) = \frac{\partial G(x,\sigma)}{\partial x} * \log(U(x)) + \frac{\partial G(x,\sigma)}{\partial x} * \log(B(x)),$$

In cases when the image derivative of the bias field is close to zero, the image derivative of the observed image will approximate the image derivative of the true, unobserved image in the additive model $$\frac{\partial G(x,\sigma)}{\partial x} * \log(I(x)) \approx \frac{\partial G(x,\sigma)}{\partial x} * \log(U(x))$$

$$\text{s.t. } \frac{\partial G(x,\sigma)}{\partial x} * \log(B(x)) \approx 0.$$

As a consequence, the filter responses of a Gaussian derivative-based filter at scale σ will be invariant to bias fields that have sufficiently small image derivatives (compared to the true image derivatives) at that scale. The implication of this is that a descriptor of the invention relying solely on first- and second-order image derivatives, will be invariant to such multiplicative bias fields when applied to log(I).

Although seven particular base filters are used as described above, one can vary this by using more, fewer and/or different base filters. The filters of course should not capture zero-order information.

In general, a combination of log(I) and linear filters that integrate to zero (this is the case for the 7 filters described above) can be used. Other linear filters (that integrate to zero) include
  Gaussian derivatives of order higher than zero (such as first-order derivative, second-order derivative) and combinations thereof [7] different from the ones considered in the example below.
  Haar wavelet functions [16],
  Gabor filters with odd functions in the Fourier domain [17].
  Another type of filters that can be used directly on I is non-linear filter banks that are invariant to monotonic intensity transformations. These include local binary patterns (LPB) [18].

Texture Classifier

To utilise the texture-based biomarker of the invention as a prognostic biomarker, a classifier may be used as now described. By way of example, the concatenated histograms may be used as input features x to a support vector machine (SUM) [9]. The SVM discriminant function $$f(x) = \sum_{i=1}^{N} a_i k(x_i, x) + b$$

may be used for texture scoring. It is determined by solving $$\underset{a \in \mathbb{R}^N, b \in \mathbb{R}}{\text{minimize}} \sum_{i=1}^{N} L_{hinge}(y_i, f(x_i)) + \frac{1}{2C}\|f\|^2$$

where $y_i \in \{-1,1\}$ encodes the class label of training pattern $x_i \in \chi$ (i=1, . . . , N). The loss function is defined as
$L_{hinge}(y,\hat{y})=\max(0,1-y\hat{y})$
and $$\|f\|^2 = \sum_{i=1, j=1}^{N} a_i a_j k(x_i, x_j)$$

The radial Gaussian kernel was used, $k(x_i, x)=\exp(-\gamma\|x_i-x\|^2)$, and the regularization parameter C>0 and the kernel parameter γ>0 were selected by grid search. We considered the following hyperparameter values in the grid: $\log(C) \in \{0,1, \ldots, 10\}$ and $\log(\gamma) \in \{\log(\gamma_{jaakkola})-4+1/3\text{ i}\}_{i=0,1,\ldots,24}$ where $\gamma_{Jaakkola}=\text{median}\{\min\{\|x_i-x_j\|\|(x_j, y_j) \in S \land y_i \neq y_j\}|(x_i, y_i) \in S\}$ provides an initial guess for γ [19] around which the grid search was centred. The performance of each parameter combination in the grid may be estimated by 20-fold cross-validation, splitting the available training data stratified by class label. The hyperparameter combination (C,γ) resulting in the lowest cross-validation area under the receiver operating characteristic (ROC) curve (AUC) is selected and the SVM is finally trained on the complete training set using these parameters.

The invention will be further described and illustrated by the following example making reference to the appended drawing in which:—

FIG. 1 shows scatter plots of test set texture scores in original MRIs versus bias corrected MRIs. Panel (A) Texture scores obtained using GFBZERO. Panel (B) Texture scores obtained using GFB. The full line is the identity line.

EXAMPLE 1

In this example, a proposed descriptor of the invention is compared to an alternative bias field variant version where the Gaussian function is kept in the descriptor and MRI images are not log transformed.

We used the baseline T1-weighted "complete annual year 2 visits" 1.5-T MRI dataset 2.5 from the collection of standardized datasets released by the Alzheimer's Disease Neuroimaging Initiative (ADNI) [11]. The dataset definition was downloaded from the ADNI website (http://adni.loni.usc.edu/methods/mri-analysis/adni-standardized-data/) on Sep. 28, 2012. The dataset comprises 504 persons, 169 normal controls (NC), 234 subjects with MCI, and 101 AD patients.

Two datasets were defined, a training set comprising all NCs and ADs, and a test set comprising all MCIs. The MCIs in the test set were labeled according their two year follow-up diagnosis; stable (had a NC or MCI diagnosis at follow-up) or converter (had an AD diagnosis at follow-up). The training set was used for method training, and the test set was used to evaluate the consistency of the methods.

We consider the hippocampus as ROI in the following experiments because it is affected early in the AD disease process and because it is generally severely affected [12, 13]. The left and right hippocampus were segmented using cross-sectional FreeSurfer [14], and the hippocampi were jointly used as ROI. Prior to computing the texture descriptor, the segmentation was post-processed using morphological erosion with a spherical structuring element of radius 1 mm in order to remove noise from the segmentation boundary and ensure that texture was computed in the interior of the hippocampus.

The number of histogram bins was determined as $$N_b = \lfloor \sqrt[3]{731} \rfloor = 9$$

in the experiments. The smallest morphologically cleaned bilateral hippocampal segmentation in the training set, which contained 731 voxels, determined this number in order to ensure an adequate number of voxels for histogram estimation.

We compare two methods that are both based on an SVM for classification. The second method is in accordance with the invention. In each case, the SVM is trained using the training set as described above. The two methods deviate in how the image data is represented and are as follows:

Gaussian derivative-based Filter Bank with Zero-order information (GFBZERO): Image data represented using the hippocampal texture descriptor described above augmented with the Gaussian function by convolving the image with the Gaussian at the same four scales as considered earlier and appending the corresponding filter response histograms to the existing representation;

$$[h_{\lambda_1(x;0.6)}, \ldots, h_{\|H(x;0.6)\|_F}, \ldots, h_{\|H(x;1.7)\|_F}] \| [h_{G(x;0.6)}, \ldots, h_{G(x;1.7)}].$$

The Gaussian function is also one of the filters used in References 3 and 4.

Prior to SVM training, the MRI images in the training set are bias field corrected using the nonparametric non-uniform intensity normalization (N3) method [2].

Gaussian derivative-based Filter Bank (GFB): log transformed image data represented using the descriptor of described in the section above. The image data is log transformed to achieve multiplicative bias field invariance as described in the section above. Note that the training data is N3 corrected and log transformed, by using log(1+I), prior to entering the SVM training. One is added to the image to avoid taking the logarithm of zero.

The two methods are applied to score two versions of the test set, the original MRIs and the N3 bias field corrected MRIs. In GFB, log(1+I) is further applied.

The consistency between texture-scores obtained on original- and N3 corrected MRIs, respectively was visually inspected by scatter plotting (see FIG. 1 panels A and B). The associated Pearson correlation coefficients were as follows (original MRIs vs. N3 corrected MRIs): Panel A (comparative) GFBZERO 0.86 and Panel B GFB 0.97. Both correlations were significant.

The prognostic stability as a function of using either original MRIs or N3 corrected MRIs of the two methods was further evaluated using ROC-analysis (see Table 1).

TABLE 1

| Diagnostic AUCs. | | |
|---|---|---|
| | Original MRIs | Bias corrected MRIs |
| GFBZERO | 0.667 | 0.693 |
| GBF | 0.719 | 0.726 |

It can be seen that a superior result is obtained according to the invention (GBF) both on original MRIs and on Bias corrected MRIs and the result achieved according to the invention is better without bias correction than is achieved according to the comparator with bias correction. Thus it is shown that using a bank of texture extracting filters, such that said filters are invariant to the presence of a multiplicative bias field gives a better result than correcting for the bias and using a set of filters that are not bias field invariant.

Another beneficial effect demonstrated by this evaluation is the "stability of prognostic performance". That is, the difference between AUCs when a method is applied to original MRIs and Bias corrected MRIs, respectively.

For GFB, the gap in AUC is small, i.e. it does not matter whether we bias correct or not. For the GFBZERO, the difference in AUC is substantially greater according to whether bias correction is applied or not. Thus, the method of the invention will be more robust against uncertainties as to whether a bias correction has been effectively applied.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

REFERENCES

1. Belaroussi, B., et al., *Intensity non-uniformity correction in MRI: existing methods and their validation*. Med Image Anal, 2006. 10(2): p. 234-46:

2. Sled, J. G., A. R. Zijdenbos, and A. G. Evans, *A nonparametric method for automatic correction of intensity nonuniformity in MRI data*. IEEE Trans Med Imaging, 1998. 17(1): p. 87-97.

3. Chincarini, A., et al., *Local MRI analysis approach in the diagnosis of early and prodromal Alzheimer's disease*. Neuroimage, 2011. 58(2): p. 469-480.

4. Chincarini, A., et al., *Automatic temporal lobe atrophy assessment in prodromal AD: Data from the DESCRIPA study*. Alzheimers Dement, 2014. 10(4): p. 456-67.

5. Sorensen, L., et al., *Texture-Based Analysis of COPD: A Data-Driven Approach*. IEEE Trans Med Imaging, 2012. 31(1): p. 70-78.

6. Nielsen, M., M. De Bruijne, and L. Sorensen, *Classification of medical diagnostic images*. 2011.

7. Lindeberg, T., Scale Space, in *Encyclopedia of Computer Science and Engineering*, 2009, John Wiley and Sons. p. 2495-2504.

8. Ojala, T., M. Pietikäinen, and D. Harwood, *A comparative study of texture measures with classification based on featured distributions.* Pattern Recognit, 1996. 29(1): p. 51-59.

9. Cortes, C. and V. Vapnik, *Support-Vector Networks.* Mach Learn, 1995. 20(3): p. 273-297.

10. Jaakkola, T., M. Diekhans, and D. Haussler. *Using the Fisher kernel method to detect remote protein homologies.* in *ISMB.* 1999. AAAI Press.

11. Wyman, B. T., et al., *Standardization of analysis sets for reporting results from ADNI MRI data.* Alzheimers Dement, 2013. 9(3): p. 332-337.

12. Braak, H. and E. Braak, *Frequency of stages of Alzheimer-related lesions in different age categories.* Neurobiol Aging, 1997. 18(4): p. 351-357.

13. West, M. J., et al., *Differences in the pattern of hippocampal neuronal loss in normal ageing and Alzheimer's disease.* Lancet, 1994. 344(8925): p, 769-772.

14. Fischl, B., et al., *Whole brain segmentation: automated labeling of neuroanatomical structures in the human brain.* Neuron, 2002. 33(3): p. 341-355.

15. DeLong, E. R., D. M. DeLong, and D. L. Clarke-Pearson, *Comparing the areas under two or more correlated receiver operating characteristic curves: a nonparametric approach.* Biometrics, 1988. 44(3): p. 837-845.

16. Porwik P., Lisowska A., *The Haar-Wavelet Transform in Digital Image Processing: Its Status and Achievements,* Machine Graphics & Vision, Vol. 13, No. 1/2, pp. 79-98, 2004.

17. Turner, M. R., Texture discrimination by Gabor functions. Biol Cybern, 1986. 55(2-3): p. 71-82.

18. Ojala, T., et al., Multiresolution Gray-Scale and Rotation Invariant Texture Classification with Local Binary Patterns. IEEE Trans Pattern Anal Mach Intell, 2002. 24(7): p. 971-987.

19. Petersen, R. C., Mild cognitive impairment as a diagnostic entity. J Intern Med, 2004. 256(3): p. 183-194.

The invention claimed is:

1. A method of analysis of a data set representing an image, said image has a multiplicative bias field in intensity, the method comprising:
   using a processor, extracting a texture based measure from the image by applying to said data set a texture extracting filter that is invariant to the presence of a multiplicative bias field;
   wherein the image is a medical image and said texture based measure is a biomarker.

2. The method as claimed in claim 1, wherein the texture extracting filter is one of three eigenvalues of a Hessian matrix defined by:

$$\lambda_i(x;\sigma), i=1,2,3, |\lambda_1| \geq |\lambda_2| \geq |\lambda_3|$$

where $x=[x, y, z]^T$ is a voxel and the Hessian matrix is defined as $$H(x;\sigma) = \begin{bmatrix} I_{xx,\sigma} & I_{xy,\sigma} & I_{xz,\sigma} \\ I_{xy,\sigma} & I_{yy,\sigma} & I_{yz,\sigma} \\ I_{xz,\sigma} & I_{yz,\sigma} & I_{zz,\sigma} \end{bmatrix}.$$

3. The method as claimed in claim 2, wherein extracting the texture based measure is by further applying the other two eigenvalues of the Hessian matrix as texture extracting filters.

4. The method as claimed in claim 1, wherein the texture extracting filter is a gradient magnitude defined by:

$$\|\nabla G(x;\sigma)\|_2 = \sqrt{I_{x,\sigma}^2 + I_{y,\sigma}^2 + I_{z,\sigma}^2}.$$

5. The method as claimed in claim 1, wherein the texture extracting filter is a Laplacian of a Gaussian defined by:

$$\nabla^2 G(x;\sigma) = \lambda_1(x;\sigma) + \lambda_2(x;\sigma) + \lambda_3(x;\sigma).$$

6. The method as claimed in claim 1, wherein the texture extracting filter is a Gaussian curvature defined by:

$$K(x;\sigma) = \lambda_1(x;\sigma)\lambda_2(x;\sigma)\lambda_3(x;\sigma).$$

7. The method as claimed in claim 1, wherein the texture extracting filter is a Frobenius norm of a Hessian matrix defined by:

$$\|H(x;\sigma)\|_F = \sqrt{\lambda_1(x;\sigma)^2 + \lambda_2(x;\sigma)^2 + \lambda_3(x;\sigma)^2}.$$

8. The method as claimed in claim 1, wherein the texture extracting filter is applied at multiple scales a.

9. The method as claimed in claim 8, wherein said scales a lie in a range from 0.3 to 25 mm.

10. The method as claimed in claim 8, wherein said scales a lie in a range from 0.3 to 2.5 mm.

11. The method as claimed in claim 8, wherein said scales a lie in a range from 0.3 to 25 µm.

12. The method as claimed in claim 1, wherein extracting the texture based measure is by applying multiple texture extracting filters at N scales, where N is computed using:

$$N = \frac{1}{p}\log_2\left(\frac{\sigma_{high}}{\sigma_{low}}\right) + 1.$$

13. The method as claimed in claim 1, wherein extracting the texture based measure is by applying from 3 to 8 texture extracting filters at 1 to 25 scales.

14. The method as claimed in claim 1, wherein extracting the texture based measure is by applying multiple texture extracting filters and concatenating histograms of filter responses of the multiple texture extracting filters.

15. The method as claimed in claim 14, wherein the histograms of filter responses are estimated using fixed binning, adaptive binning, or soft assignments as in locally orderless images.

16. The method as claimed in claim 1, further comprising labeling said image as being included in a class of images by applying a statistical classifier to said texture based measure.

17. The method of claimed in claim 1, wherein the image is an MRI image.

18. The method as claimed in claim 17, wherein the MRI image is of a brain or part thereof.

19. The method as claimed in claim 18, wherein the image derives from a person with mild cognitive impairment (MCI).

20. The method as claimed in claim 19, further comprising labeling said image according to a likelihood of the person progressing from MCI to increased severity of dementia, by applying a statistical classifier to said biomarker.

21. The method as claimed in claim 20, wherein said increased severity of dementia is Alzheimer's disease.

22. A computer program product comprising a non-transitory computer readable medium having instructions recorded thereon, the instructions when executed by a computer system implementing the method of claim 1.

23. The method as claimed in claim 1, wherein the biomarker comprises a multi-dimensional representation that characterizes texture of the image.

\* \* \* \* \*